United States Patent [19]
Diamond et al.

[11] 3,979,428
[45] Sept. 7, 1976

[54] PHENYLACETIC ACIDS

[75] Inventors: Julius Diamond, Lafayette Hill; Norman Julian Santora, Roslyn, Pa.

[73] Assignee: William H. Rorer, Inc., Fort Washington, Pa.

[22] Filed: June 24, 1975

[21] Appl. No.: 589,748

Related U.S. Application Data

[60] Continuation of Ser. No. 423,542, Dec. 10, 1973, abandoned, which is a division of Ser. No. 152,451, June 11, 1971, Pat. No. 3,821,267, which is a continuation-in-part of Ser. No. 34,870, May 5, 1970, Pat. No. 3,864,384.

[52] U.S. Cl. ............................................. 260/455 A
[51] Int. Cl.² ........................................ C07C 155/02
[58] Field of Search ................................ 260/455 A

[56] References Cited
UNITED STATES PATENTS
3,894,080   7/1975   Diamond et al. ............... 260/455 A

*Primary Examiner*—Lewis Gotts
*Assistant Examiner*—D. R. Phillips
*Attorney, Agent, or Firm*—Erich M. H. Radde

[57] ABSTRACT

Novel p-cycloalkylphenylacetic acids which are substituted in α-position by a carbamylthio, loweralkylcarbamylthio, or diloweralkylcarbamylthio group, and their salts have been prepared. They possess useful antiinflammatory, analgesic, and antipyretic properties.

5 Claims, No Drawings

PHENYLACETIC ACIDS

CROSS REFERENCES TO RELATED APPLICATIONS

This is a continuation of application Ser. No. 423,542, now abandoned, filed Dec. 10, 1973, which is a divisional application of App. Ser. No. 152,451, filed 6-11-71, now U.S. Pat. No. 3,821,267 which is a continuation-in-part application of Ser. No. 34,870 now U.S. Pat. No. 3,864,384 filed May 5, 1970.

SUMMARY OF THE INVENTION

This invention describes certain $\alpha$-carbamylthio-p-cycloalkylphenylacetic acids and their derivatives and their use in therapeutic compositions. In addition, this invention relates to the preparation of these $\alpha$-mercapto-p-cycloalkylphenylacetic acids. When the compounds of this invention are administered to mammals, they afford significant treatment of inflammation and associated pain and fever.

They further provide analgesic and antipyretic methods for the relief and treatment of pain and fever associated with inflammation.

BACKGROUND OF THE INVENTION

There has been continued efforts in research to develop drugs which would significantly inhibit the development of inflammation and relieve the pain and fever associated with it. Much of these efforts have been carried on in the field of steroids. While many of these compounds have been effective, they have had the drawback of causing many side effects.

We have unexpectedly found that $\alpha$-carbamylthio-p-cycloalkylphenylacetic acid compounds and their derivatives have valuable pharmacologic properties.

We have found that $\alpha$-carbamylthio-p-cycloalkylphenylacetic acid compounds and their derivatives possess useful anti-inflammatory, analgesic and antipyretic properties.

We have also found a series of anti-inflammatory compounds which are non-steroidal.

We have further found that these $\alpha$-carbamylthio-p-cycloalkylphenylacetic acid compounds and their derivatives are novel.

We have also found that the compounds of this invention are useful in effectively providing a method for the inhibition of inflammation and the treatment of associated pain and fever.

We have still further found an entirely new class of anti-inflammatory, analgesic and antipyretic pharmaceutical compositions containing the $\alpha$-carbamylthio-p-cycloalkylphenylacetic acids and derivatives of this invention as active ingredient.

We have again found a convenient method for synthesizing these compounds.

DESCRIPTION AND PREFERRED EMBODIMENT

This invention comprises a class of novel chemical compounds which contain a cycloalkyl radical which is attached to a substituted phenyl -$\alpha$-carbamylthioacetic acid in the para-position. This invention further comprises derivatives of said acetic acids and the method of preparing the same.

This invention also describes a new method of treating inflammation and associated pain and fever as well as novel therapeutic compositions.

The compounds of this invention contain an asymmetric carbon atom in the alpha-position of the acetic acid side chain. As a result, the above compounds of formula I may be obtained as racemic mixtures of their dextro (+) and levorotatory (−) isomers. It is to be understood that said $d$ and $l$ isomers as well as the dl mixtures thereof are embraced within the scope of this invention.

When B is loweralkyl, two racemic mixtures may exist in the case of 2'- or 3'-loweralkylcyclohexylphenyl-$\alpha$ carbamylthioacetate or their derivatives. It is understood that both racemic mixtures are embraced within the scope of this invention.

The preferred R and R' substituents are in the 3 and 5 positions.

The preferred compounds of this embodiment describe the cyclohexyl class of chemical compounds which have particular usefulness as anti-inflammatory, analgesic and antipyretic agents. These compounds are where:

R is halo or nitro;
R' is hydrogen, chloro, bromo or nitro;
X is carbamylthio, loweralkylcarbamylthio, or diloweralkylcarbamylthio;
and
Z is -OH or
OM where M is an alkali, alkaline earth, or aluminum metal or an ammonium salt.

The most preferred compounds of this invention describe a class of chemical compounds which have particular usefulness as anti-inflammatory, analgesic and antipyretic agents.

Included within the scope of this further special embodiment are the racemic mixtures as well as the dextro and levorotatory isomers thereof.

In the descriptive portions of this invention, the following definitions apply:

The preferred "alkali" or "alkaline" metals are sodium, potassium, calcium and magnesium.

The term "ammonium salt" refers to the cation formed when ammonia or an organic amine react with the carboxyl group to form ammonium salts of the structure given in the formula. The ammonium salts are formed with a (1) loweralkylamines such as methylaminel, diethylamine, triethylamine; (2) hydroxyloweralkylamines such as $\beta$-hydroxyethylamine, (3) heterocyclic amines such as 2-aminopyridine, piperazine, piperidine; (4) aralkylamines such as $\alpha$-methylbenzylamine, phenethylamine; (5) cycloalkylamines such as cyclohexylamine; (6) alkaloids such as quinine, cinchonidine, cinchonine, ephedrine.

Representative compounds of this invention which are particularly useful are as follows:

$\alpha$-carbamylthio-3-chloro-4-cyclohexylphenylacetic acid
$\alpha$-ethylcarbamylthio-3-chloro-4-cyclohexylphenylacetic acid
$\alpha$-dimethylcarbamylthio-3-chloro-4-cyclohexylphenylacetic acid
$\alpha$-diethylcarbamylthio-3-chloro-4-cyclohexylphenylacetic acid
$\alpha$-diethylcarbamylthio-3,5-dichloro-4-cyclohexylphenylacetic acid
$\alpha$-ethylcarbamylthio-3-chloro-5-bromo-4-cyclohexylphenylacetic acid
d $\alpha$-diethylcarbamylthio-3,5-dichloro-4-cyclohexylphenylacetic acid α-diethylcarbamylthio-3,5-dichloro-4-cyclohexylphenylacetic acid The α-mercapto-p-cycloalkylphenylacetic acid may then be reacted with a loweralkyl chlorocarbonate, an alkali isocyanate in the presence of hydrogen chloride, a loweralkylcarbamyl chloride or a diloweralkylcarbamyl chloride to form the corresponding α-mercaptoacetic acid derivative. The α-mercapto-p-cycloalkylphenylacetic acid may also be reacted with succinic anhydride, maleic anhydride or phthalic anhydride to form the corresponding derivative.

Of course it will be understood by one skilled in the art that variations in the above procedures can be employed which will give that sequence of reactions which will result in the desired R, R′, X and Z substituents.

These and other equivalent methods for the preparation of the α-carbamylthio derivatives of the present invention will be apparent to those having ordinary skill in the art.

The products of this invention may be obtained as racemic mixtures of their dextro and levorotatory isomers. These may be separated by any of the various methods of resolution. One method that may be employed is combining the racemic compound with an optically active compound by salt formation, ester formation, or amide formation to form two diastereomeric products. If the instant acids are added to an optically active base, then two diastereomeric salts are produced which possess different properties and different solubilities and can be separated by fractional crystallization. When the salts have been completely separated by repeated crystallization, the base is split off by acid hydrolysis and the pure d or l acids are obtained. Preferably, an α-carbamylthio derivative of a cycloalkylphenylacetic acid is reacted in alcoholic or acetone solution with an equivalent amount of the optically active primary, secondary or tertiary amine such as cinchonidine, cinchonine, quinine, ephedrine, α-methylbenzylamine, sec-butylamine, sec-amylamine, etc. The diastereomeric amine salts produced thereby, are separated by fractional crystallization and each optically active salt is hydrolyzed with dilute mineral acid to produce the dextro or levo form of the α-carbamylthio derivative of the cycloalkylphenylacetic acid. Alternatively, an α-carbamylthio derivative of a cycloalkylphenylacetate ester may be reacted with an optically active primary or secondary amine such as ephedrine, α-methylbenzylamine, secbutylamine, etc., to produce a mixture of diastereomeric acetamides which may be separated by fractional crystallization.

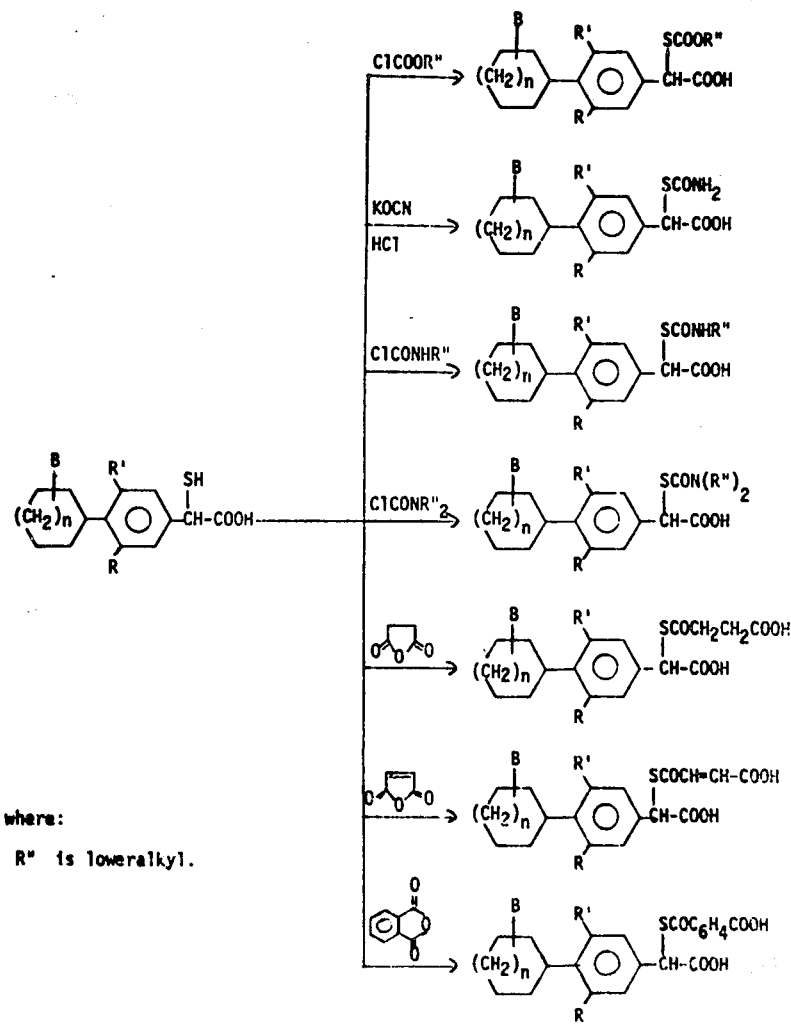

where:
R″ is loweralkyl.

Each optically active amide may be hydrolyzed with mineral acid to its respective optically active acid.

Still alternatively, an α-carbamylthio derivative of a cycloalkylphenylacetate may be reacted with an optically active alcohol such as l-menthol or d-borneol, or l-α-methylbenzylalcohol, to produce a mixture of diastereomeric acetate esters which may be separated by fractional crystallization. Each optically active ester may be hydrolyzed with mineral acid or alkali to its respective optically active acid. The optically active acids can also be recovered from the α-methylbenzyl esters by hydrogenolysis in the presence of palladium.

The resolution may also be carried out as above on the starting glycolic acid, ester or amide. The optical isomer in turn may then be converted to the α-halo compound which is then reacted as above to give the α-carbamylthio derivatives.

The racemic chloroacetic acids, esters and amides may also be resolved into their optical isomers by the processes described for the -carbamylthio acids, esters and amides.

We have found that the compounds of this invention exercise a useful degree of anti-inflammatory activity in mammals and are effective in the treatment of associated pain and fever and in like conditions which are responsive to treatment with anti-inflammatory agents. In general, the compounds of this invention are indicated for a wide variety of mammalian conditions where the symptoms of inflammation and associated fever and pain are manifested. Exemplary of such conditions are: rheumatic diseases such as rheumatoid arthritis, osteoarthritis and other degenerative joint diseases; soft-tissue rheumatism such as tendinitis; muscular rheumatism such as sciatica; pain and inflammation associated with dental surgery and similar human and veterinary disease conditions exhibiting the foregoing symptoms requiring the use of an anti-inflammatory, analgesic and/or antipyretic agent.

For these purposes, the compounds of this invention are normally administered orally, topically, parenterally or rectally. Orally, these may be administered in tablets, capsules, suspensions or syrups; the optimum dosage, of course, depending on the particular compound being used and the type and severity of the condition being treated. In any specific case the appropriate dosage selected will further depend on factors of the patient which may influence response to the drug; for example, general health, age, weight, etc. Although the optimum quantities of the compounds of this invention to be used in such manner will depend on the compound employed and the particular type of disease condition treated, oral dose levels of preferred compounds when administered to a mammal in dosages of 0.5 to 100 milligrams per kilogram of body weight per day are particularly useful. The preferred range is 0.5 to 15 mg/Kg. Comparative dosages may be used in topical, parenteral or rectal administration.

Dosage forms may be prepared according to any method known to the art for the manufacture of pharmaceutical compositions and such compositions may contain one or more agents; for example, sweetening agents, flavoring agents, coloring agents, preserving agents, etc. Further, the active α-carbamylthio-p-cycloalkylphenylacetic acids or their derivatives may be administered alone or in admixture with antacids such as sodium bicarbonate, magnesium carbonate, magnesium hydroxide, aluminum hydroxide, magnesium silicate, etc., and non-toxic pharmaceutically acceptable excipients. Such excipients may be, for example, inert diluents such as calcium carbonate, lactose, etc., granulating and disintegrating agents; for example maize starch, alginic acid, etc., lubricating agents; for example, magnesium stearate, talc, etc., binding agents; for example, starch gelatin, etc., suspending agents; for example, methylcellulose, vegetable oil, etc., dispersing agents; for example, lecithin, etc., thickening agents; for example, beeswax, hard paraffin, etc., emulsifying agents; for example, naturally-occurring gums, etc., and non-irritating excipients; for example, cocoa butter and polyethylene glycols.

Various tests in animals can be carried out to show the ability of the α-carbamylthio-p-cycloalkylphenylacetic acids and derivatives of this invention to exhibit reactions that can be correlated with anti-inflammatory activity in humans. One such test is the Carrageenan paw edema test, which shows the ability of the instant compounds to inhibit edema induced by injection of an inflammatory agent such as carrageenan into the tissues of the paw of a rat against non-inflamed controls. This carrageenan testing method is known to correlate well with anti-inflammatory activity in humans and is a standard test used to determine anti-inflammatory activity. This correlation can be shown by the activities of compounds known to be clinically active including such as aspirin, phenylbutazone, cortisone, hydrocortisone and prednisolone. In view of the results of this test, the α-carbamylthio-p-cycloalkylphenylacetic acids and derivatives can be considered to be active anti-inflammatory agents.

One method for measuring the pain threshold of the α-carbamylthio-p-cycloalkylphenylacetic acids and derivatives is the Randall-Selitto test. Analgesic activity is shown by antinocieceptive testing of the inflamed foot of rats and a measurement of their pain response.

Antipyretic assay is carried out by yeast-induced fever tests of subcutaneously injected rats. The measurement of rectal temperature is carried out to determine the response by the test compounds.

In view of the results of the above tests, the α-carbamylthio-p-cycloalkylphenylacetic acids and derivatives of this invention are considered to have valuable analgesic and antipyretic properties.

Other tests which can be correlated to show significant activities are the "phenylquinone writhing" test for analgesia, "polyarthritis in rats" and "ultra-violet erythema in guinea pigs".

U.S. Pat. No. 3,821,267 describes in detail the preparation of the starting materials, the methods of producing same as well as of compounding the compounds according to the present invention to useful pharmaceutical preparations, and their administration in therapy, dosage, and the like. Said patent is incorporated by reference hereinto.

The following are detailed examples which show the preparation of the compounds of this invention. They are to be construed as illustrations of said compounds and are not intended to be limitations thereof.

EXAMPLE 1

α-Diethylcarbamylthio-3-chloro-4-cyclohexylphenylacetic acid

A solution of α-mercapto-3-chloro-4-cyclohexylphenylacetic acid prepared as described in U.S. Pat. No. 3,821,267, 5.6 g. (0.2 moles) in 25 ml. of pyridine is cooled in an ice bath. To this is added dropwise 0.022 moles of diethylcarbamyl chloride. The mixture is then stirred for 2 hours, diluted with ether and filtered. The mixture is then basified with 10% sodium bicarbonate solution. The alkaline mixture is washed with ether, acidified with 10% hydrochloric acid, extracted with ether which in turn is washed with cold water, dried and evaporated to dryness. Trituration with hexane results in α-diethylcarbamylthio-3-chloro-4-cyclohexylphenylacetic acid.

When diethylcarbamylchloride is replaced in the above procedure by carbamyl chloride (prepared in situ from potassium cyanate and anhydrous hydrogen chloride in anhydrous chloroform), ethylcarbamyl chloride or dimethylcarbamyl chloride, then the products prepared are α-carbamylthio-3-chloro-4-cyclohexylphenylacetic acid, α-ethylcarbamylthio-3-chloro-4-cyclohexylphenylacetic acid or α-dimethylcarbamylthio-3-chloro-4-cyclohexylphenylacetic acid.

When the α-mercaptoacetic acids, esters and amides of this invention are used in the above procedure then the corresponding α-carbamylthioacetic acids, esters and amides are prepared.

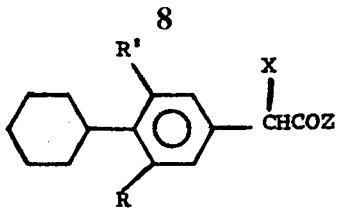

where
R is halo or nitro;
R' is hydrogen, chloro, bromo, or nitro;
X is carbamylthio, loweralkylcarbamylthio, or diloweralkylcarbamylthio; and
Z is —OH, or
—OM where M is an alkali, alkaline earth or aluminum metal or an ammonium salt.

2. α-Carbamylthio-3-chloro-4-cyclohexylphenylacetic acid.

3. α-Ethylcarbamylthio-3-chloro-4-cyclohexylphenylacetic acid.

4. α-Dimethylcarbamylthio-3-chloro-4-cyclohexylphenylacetic acid.

Example 2

When the procedures of Examples 1–68 are followed but using the starting materials below, then the corresponding products are obtained.

| STARTING MATERIAL | PRODUCT | EXAMPLE |
|---|---|---|
| α,3,5-trichloro-4-cyclohexylphenylacetic acid | α-diethylcarbamylthio-3,5-dichloro-4-cyclohexylphenylacetic acid | 55,66 |
| α,3-dichloro-5-bromo-4-cyclohexylphenylacetic acid | α-ethylcarbamylthio-3-chloro-5-bromo-4-cyclohexylphenylacetic acid | 55,66 |
| α,3,5-trichloro-4-cyclopentylphenylacetic acid | α-diethylcarbamylthio-3,5-dichloro-4-cyclopentylphenylacetic acid | 55,66 |
| α-diethylcarbamylthio-3,5-dichloro-4-cyclohexylphenylacetic acid | d α-diethylcarbamylthio-3,5-dichloro-4-cyclohexylphenylacetic acid | 32 |
| α-diethylcarbamylthio-3,5-dichloro-4-cyclohexylphenylacetic acid | l α-diethylcarbamylthio-3,5-dichloro-4-cyclohexylphenylacetic acid | 31 |
| α-i-propylthio-3-chloro-5-nitro-4-cyclohexylphenylacetic acid | d α-i-propylthio-3-chloro-5-nitro-4-cyclohexylphenylacetic acid | 32 |
| α-i-propylthio-3-chloro-5-nitro-4-cyclohexylphenylacetic acid | l α-i-propylthio-3-chloro-5-nitro-4-cyclohexylphenylacetic aci | 31 |
| α-propionylthio-3-chloro-4-cyclohexylphenylacetic acid | d α-propionylthio-3-chloro-4-cyclohexylphenylacetic acid | 32 |
| α-propionylthio-3-chloro-4-cyclohexylphenylacetic acid | l α-propionylthio-3-chloro-4-cyclohexylphenylacetic acid | 31 |
| α-sulfino-3-nitro-4-cyclohxylphenylacetic acid | d α-sulfino-3-nitro-4-cyclohexylphenylacetic acid | 32 |
| α-sulfino-3-nitro-4-cyclohxylphenylacetic acid | l α-sulfino-3-nitro-4-cyclohexylphenylacetic acid | 31 |
| α-methylsulfinyl-3,5-dichloro-4-cyclohexlphenylacetic acid | d α-methylsulfinyl-3,5-dichloro-4-cyclohexylphenylacetic acid | 32 |
| α-methylsulfinyl-3,5-dichloro-4-cyclohexylphenylacetic acid | l α-methylsulfinyl-3,5-dicloro-4-cyclohexylphenylacetic acid | 31 |
| α-(σ-carboxybenzoylthio)-3-chloro-5-nitro-4-cyclohexylphenylacetic acid | d α-(p-carboxybenzoylthio)-3-chloro-5-nitro-4-cyclohexylphenylacetic acid | 32 |
| α-(σ-carboxybenzoylthio)-3-chloro-5-nitro-4-cyclohexylphenylacetic acid | l α-(p-carboxybenzoylthio)-3-chloro-5-nitro-4-cyclohexylphenylacetic acid | 31 |
| α-diethylcarbamylthio-3-chloro-4-cyclopentylphenylacetic acid | d α-diethylcarbamylthio-3-chloro-4-cyclopentylphenylacetic acid | 32 |
| α-diethylcarbamylthio-3-chloro-4-cyclopentylphenylacetic acid | l α-diethylcarbamylthio-3-chloro-4-cyclopentylphenylacetic acid | 31 |
| α-diethylcarbamylthio-3-chloro-4-cycloheptylphenylacetic acid | d α-diethylcarbamylthio-3-chloro-4-cycloheptylphenylacetic acid | 32 |
| α-diethylcarbamylthio-3-chloro-4-cycloheptylphenylacetic acid | l α-diethylcarbamylthio-3-chloro-4-cycloheptylphenylacetic acid | 31 |

We claim:
1. A compound of the formula

5. α-Diethylcarbamylthio-3-chloro-4-cyclohexylphenylacetic acid.

* * * * *